United States Patent [19]
Stockmeier

[11] Patent Number: 5,195,956
[45] Date of Patent: Mar. 23, 1993

[54] MEDICAL CATHETER WITH A CUTTING DEVICE

[76] Inventor: Uwe Stockmeier, Heimgartenstr. 15, 8132 Tutzing, Fed. Rep. of Germany

[21] Appl. No.: 536,561

[22] Filed: Sep. 19, 1990

Related U.S. Application Data

[63] Continuation at PCT/EP89/00054, Jan. 18, 1989.

[30] Foreign Application Priority Data

Jan. 19, 1988 [DE] Fed. Rep. of Germany ....... 3801318

[51] Int. Cl.⁵ .................... A61B 17/22; A61B 17/32
[52] U.S. Cl. .................................. 604/22; 606/159; 606/180
[58] Field of Search .................. 606/159, 180, 170; 604/22; 128/751, 752, 755

[56] References Cited

U.S. PATENT DOCUMENTS

| | | | |
|---|---|---|---|
| 3,614,953 | 10/1971 | Moss | 606/159 |
| 4,690,140 | 9/1987 | Mecca | 606/159 |
| 4,790,813 | 12/1988 | Kensey | 606/159 X |
| 4,857,046 | 8/1989 | Stevens et al. | 606/159 X |

*Primary Examiner*—Michael H. Thaler
*Attorney, Agent, or Firm*—Helfgott & Karas

[57] ABSTRACT

In a medical catheter, a cutting device is provided, which has a rotary cutting tool positioned at a front end of a tube and which is axially displaceable relative thereto between a working position and a rest position. Each position is defined by a stop. The cutting tool is mounted on a rigid shaft received in a bearing member which interacts with the stops.

10 Claims, 1 Drawing Sheet

MEDICAL CATHETER WITH A CUTTING DEVICE

CROSS REFERENCE TO RELATED APPLICATION

This application is a continuation of International Application No. PCT/EP89/00054 filed 18 Jan. 1989.

BACKGROUND OF THE INVENTION

The invention concerns a medical catheter with a cutting device on the front end to insert into blood vessels. The cutting device has a rotary cutting tool, which has a diameter of the tube. The rotary cutting tool is movable to the front and back, but only a certain distance before it is stopped.

By this well known catheter it is disadvantageous that the position of the cutting device in relation to the front end of the tube is not definitely determined by the application of the catheter; among other disadvantageous is that, in the scope of the curved catheter the power shaft and the tube are often displaced against each other in the curvature. A cutting device which is too far out of the tube could cause undesired damage for the consequences, particularly damage to the vessel.

SUMMARY OF THE INVENTION

It is an object of this invention to reduce the unwanted damage to the tissue. This object is attained by the invention wherein the cutting device is positioned on the front end of the tube in such a way that the cutting device ist positioned in a retracted rest position where it is completely covered by the tube. In the second position, the working position, the cutting device is positioned outside the tube. The cutting device can slide axially.

Moreover there is a substantial consideration in the fact that the cutting device can be pushed out in small amounts so that the thrombosis collapses. The cutting device can be moved forward slowly to completely destroy the thrombosis the blood vessel without crashing and pressing.

The cutting tool, however, always is fixed in the center by the front end of the tube. Because the working position of the cutting tool is defined by a stop pin it is surely prevented that the vessel will be injured inadvertently by a too far advanced cutting tool.

With the newly invented catheter there is no danger that the cutting device will move too far out of the tube, as was with known catheters. The treatment takes less time as the physician needs less precision and exactness. At the same time there is no danger for the treated vessel. It is a big advantage for both patient and physician that the treatment time has been shortened.

Due to the stiff shaft it is not possible that the cutting propeller slips out to harm the vessel. The propeller cannot move diagonally, only horizontally. The cutting device can be adjusted in length, preceding the end of the tube, for each specific case.

The invention can be combined with other instruments for the treatment of visual sicknesses eg. For the dilation of vessels.

In the following two examples how to adapt the invention, using the design;

DETAILED DESCRIPTION OF THE PREFERRED EMBODIMENTS

Figure 1:
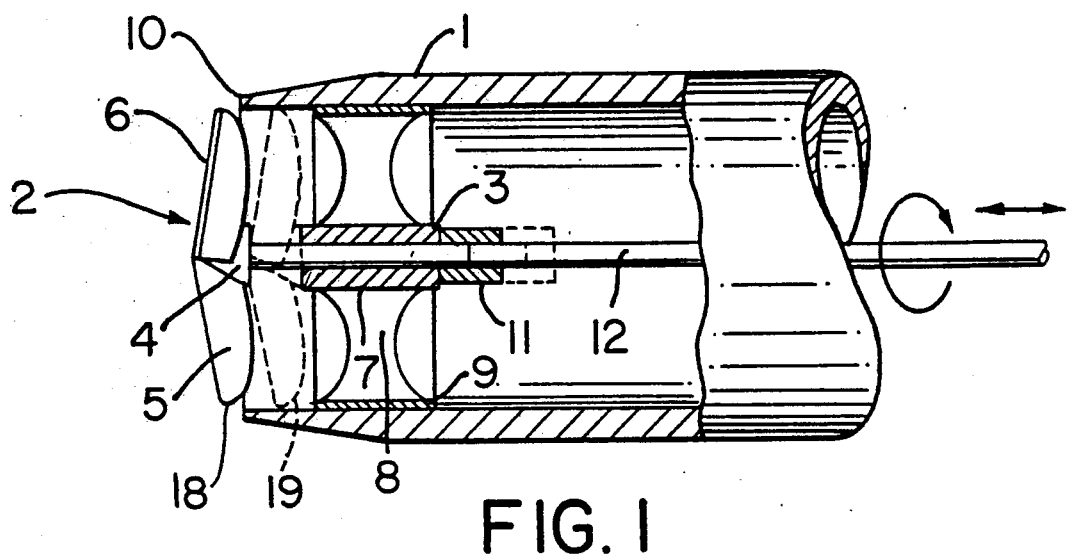
FIG. 1 shows a section through a catheter according to the invention with a mechanical drive of the cutting device.

FIG. 1 shows the front end of a tube (1), a centrally supported flexible driving shaft (12) provided in connection with a stiff or rigid shaft (3) which carries at its free end a hub (4) of a cutting tool (5).

Further is shown a sliding bearing (7) fixed in the center by the bush (9). The bush is positioned in the front end of the tube, which is bevelled towards its end and rounded off at its front to avoid the injury danger for the vessels. The position of the cutting device is determined in the working position (A) by the fact that the end of the sliding bearing (7) which is averted from the device, touches a stop pin (11).

The broken lines show the device in the rest position (R) which is determined by the fact that its hub (4) touches the end of the sliding bearing, which is turned towards the device.

Tube (1) can be designed as a suction tube connectable to a suction pump.

Figure 2:
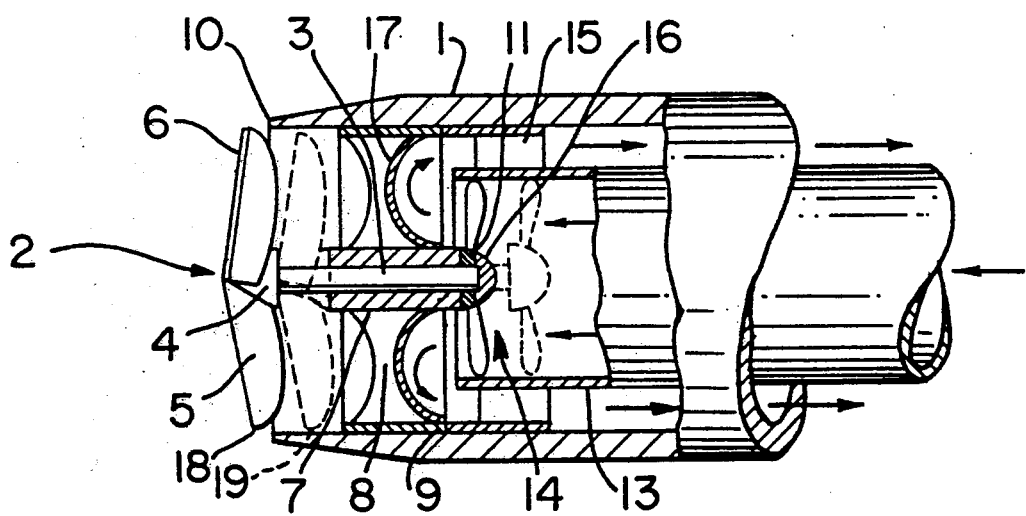
FIG. 2 shows a section through a catheter according to the invention with a hydraulic drive of the cutting device.

FIG. 2 is an alterative embodiment of the catheter according to the invention.

The cutting device in this embodiment is driven by a fluid supplying pressure, conveyed inside the tube. For this, action the tube contains a second tube (13) in which the fluid under pressure is applied to a turbine (14). The turbine is rigidly mounted to the cutting instrument by a stiff shaft (3). The end of the inner tube (13) is fixed in the center of the bush (9) by several guiding sheets (15). Here, the working position is defined by the hub of the turbine (16) which is stopped by the end of the sliding bearing averted from the cutting device. The outer periphery of the turbine fills the inside of the inner tube (13). The excess length of the cutting tool out of the front end of the tube (1) can be varied if the hub (4) of the cutting device and/or the stiff shaft (3) are exchanged for components of a greater or smaller axial extension.

I claim:

1. A medical catheter comprising a tube; a cutting device provided at a front end of said tube for introducing into blood vessels, said tube having an inner diameter, said cutting device comprising a rotary cutting tool having an outer diameter with is smaller than the inner diameter of said tube, said tool being capable of being axially shifted along an axis of rotation thereof relative to said tube between a retracted rest position in which said cutting tool is completely covered by said front end of said tube, and an extended working position in which said cutting tool protrudes from said front end of the tube; and stops so that each of said positions is defined by a stop, said cutting device further comprising a rigid shaft on which said cutting tool is mounted, and a bearing member in which said rigid shaft is received, said bearing member being located at said front end of the tube, and wherein the stops which define the working position and the rest position, respectively, of said cutting tool interact with said bearing member to define said working and rest positions.

2. Catheter according to claim 1, wherein the stop defining the working position of said cutting tool is positioned on said rigid shaft inside of said tube.

3. Catheter according to claim 1, wherein the cutting tool is formed as a cutting propeller having blades including cutting edges and being able to build up a suction towards said end of the tube.

4. Catheter according to claim 3, and further comprising a bush inserted in said tube at a front end portion thereof and positioned on said bearing member, wherein said cutting tool is mounted at an end of said rigid shaft and protrudes over said end, said rigid shaft extending in said bearing member which is arranged centrally of said bush, said bearing member being connected with said bush by spokes.

5. Catheter according to claim 1, and further comprising a flexible power shaft positioned within said tube and connected to said rigid shaft, said cutting tool being driven by said flexible power shaft via said rigid shaft so as to provide a longitudinal shifting of the cutting tool relative to said tube.

6. Catheter according to claim 1, wherein said tube is formed as a suction tube connectable to a suction pump.

7. Catheter according to claim 1, wherein one of said cutting tool and said rigid shaft is replaceable such that a portion of said cutting tool protruding beyond said front end of said tube in said working position is adjustable.

8. Catheter according to claim 1, wherein said cutting device comprises a turbine driven by a pressurizing medium introduced through said tube, said turbine being fixedly connected to said cutting tool.

9. Catheter according to claim 8, wherein said cutting device is shiftable as a whole in a direction of an axis of said tube.

10. Catheter according to claim 9, wherein said tube comprises two chambers, one of said chambers applying the pressurizing medium, and another of said chamber providing a backflow of said medium, whereby a shifting movement of the cutting device takes place when a pressure flow of the pressurizing medium is reversed.

* * * * *